(12) United States Patent
Ye et al.

(10) Patent No.: US 11,293,239 B2
(45) Date of Patent: Apr. 5, 2022

(54) TREATMENT OF OIL-BASED MUD FOR DETERMINING OIL-WATER RATIO

(71) Applicant: HALLIBURTON ENERGY SERVICES, INC., Houston, TX (US)

(72) Inventors: Xiangnan Ye, Cypress, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 190 days.

(21) Appl. No.: 16/754,686

(22) PCT Filed: Jun. 7, 2019

(86) PCT No.: PCT/US2019/036088
§ 371 (c)(1),
(2) Date: Apr. 8, 2020

(87) PCT Pub. No.: WO2020/246992
PCT Pub. Date: Dec. 10, 2020

(65) Prior Publication Data
US 2021/0404271 A1    Dec. 30, 2021

(51) Int. Cl.
*E21B 21/06*        (2006.01)
*G01N 27/22*        (2006.01)

(52) U.S. Cl.
CPC ......... *E21B 21/062* (2013.01); *G01N 27/221* (2013.01)

(58) Field of Classification Search
CPC ..... E21B 21/062; G01N 27/221; G01N 27/06
See application file for complete search history.

(56) References Cited

U.S. PATENT DOCUMENTS

| 3,308,894 | A | * | 3/1967 | Reinhart ................. E21B 21/16 |
| | | | | 175/68 |
| 5,140,527 | A | | 8/1992 | Jones et al. |
| 6,668,929 | B2 | | 12/2003 | Griffith et al. |
| 9,719,328 | B2 | | 8/2017 | Al-Buraik |
| 2007/0012441 | A1 | | 1/2007 | Heathman et al. |
| 2011/0000713 | A1 | * | 1/2011 | Meeten ................. E21B 47/113 |
| | | | | 175/40 |

(Continued)

FOREIGN PATENT DOCUMENTS

| WO | 2019067708 | 4/2019 |
| WO | 2020139352 | 7/2020 |

OTHER PUBLICATIONS

Adeyemo, et al., "Adsorption of Dyes Using Different Types of Clay: A Review", Appl Water Sci vol. 7, 2017, pp. 543-568.

(Continued)

*Primary Examiner* — D. Andrews
(74) *Attorney, Agent, or Firm* — Kilpatrick Townsend & Stockton LLP

(57) ABSTRACT

Apparatuses and methods measure a specified volume of a drilling fluid for a test sample. An electrical parameter of the test sample is measured; and a chemical formulated to effect a change in the electrical parameter of the test sample is added in known increments. After each incremental addition of the chemical, the electrical parameter of the test sample is measured to determine if the electrical parameter measurement is at a stable value. When the electrical parameter measurement is at a stable value, the electrical parameter is correlated with an amount of water in the drilling fluid.

20 Claims, 5 Drawing Sheets

(56) References Cited

U.S. PATENT DOCUMENTS

| | | | |
|---|---|---|---|
| 2015/0268374 A1 | 9/2015 | Rapoport | |
| 2017/0321504 A1* | 11/2017 | Ye | E21B 21/06 |
| 2017/0350740 A1* | 12/2017 | Mohr | G01F 15/001 |

OTHER PUBLICATIONS

Canan, "Dielectric Properties of Mixtures of Clay-Water-Organic Compounds", (thesis submitted to the Faculty and the Board of Trustees of the Colorado School of Mines), Mar. 3, 1999, 371 pages.

PCT/US2019/036088, "International Search Report and Written Opinion", dated Mar. 5, 2020, 10 pages.

Vralstad, et al., "Dielectric Properties of Crude Oil Components", Energy&Fuels, vol. 23, Oct. 6, 2009, pp. 5596-5602.

\* cited by examiner

TREATMENT OF OIL-BASED MUD FOR DETERMINING OIL-WATER RATIO

TECHNICAL FIELD

The present disclosure relates generally to monitoring drilling fluid characteristics. More specifically, but not by way of limitation, this disclosure relates to systems and methods for real-time measurement of an oil-water ratio of oil-based drilling fluids.

BACKGROUND

A well system can include a wellbore drilled through a subterranean formation for extracting a target fluid (e.g., oil or gas) from the subterranean formation. On a drilling rig, drilling fluid is pumped from a tank or reservoir at the surface through the drill string where it sprays out of nozzles on the drill bit, cleaning and cooling the drill bit in the process. The drilling fluid then carries the crushed rock up an annular space between the drill string and the sides of the hole being drilled and emerges back at the surface where the crushed rock is filtered out, and the drilling fluid returns to the reservoir. The drilling fluid is then pumped back down and is continuously recirculated.

The drilling fluid is tested and treated periodically in the reservoir to give it properties that optimize and improve drilling efficiency. Conventional test procedures are time consuming, resulting in less testing and treatment of the drilling fluid.

DETAILED DESCRIPTION

Figure 1:
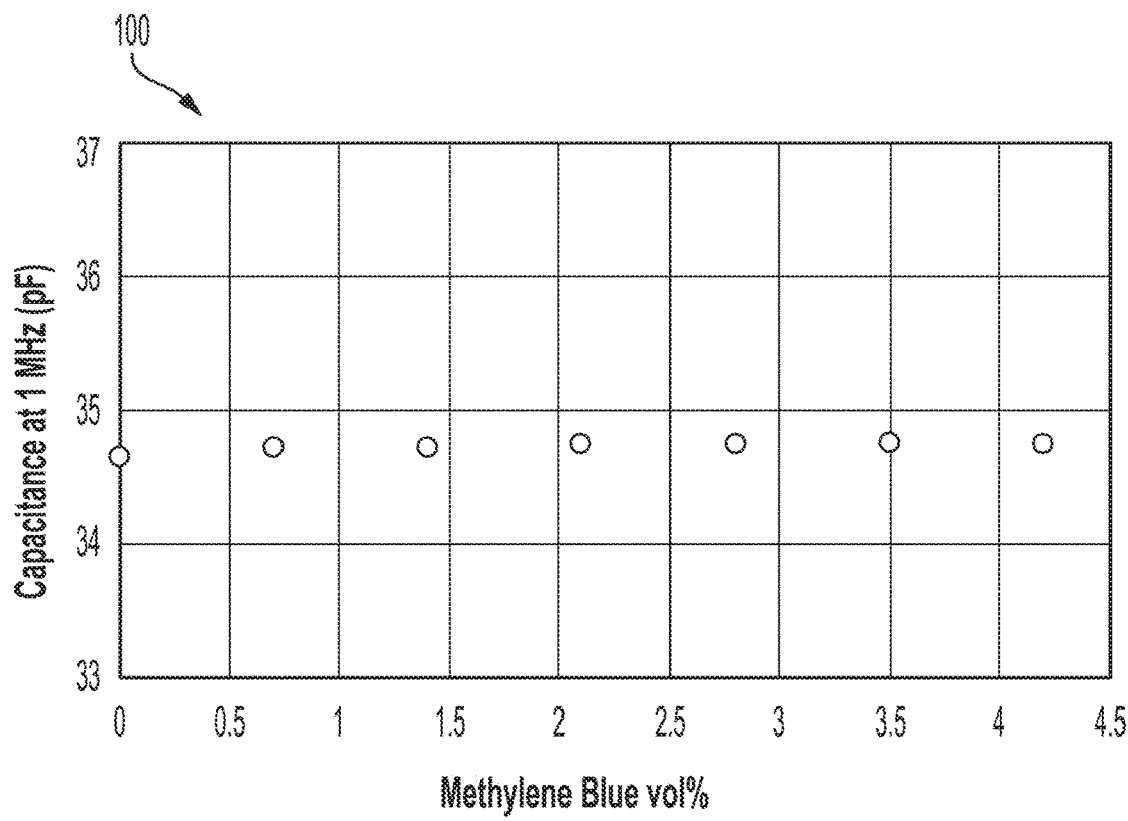
FIG. 1 is a graph illustrating capacitance measurements of an oil-based mud (OBM) sample containing no active clay according to various aspects of the present disclosure.

Certain aspects and features of the present disclosure relate to measuring and monitoring drilling fluid characteristics. Drilling fluids are mixtures of natural and synthetic chemical compounds used to cool and lubricate the drill bit, clean the hole bottom, carry cuttings (i.e., crushed rock) to the surface, control formation pressures, and improve the function of the drill string and tools in the hole. In some cases, the cuttings can deposit fine particles of electrically active clay (referred to herein as active clay) in the drilling fluid. These fine particles of active clay can skew results of electrical characterization tests, for example capacitance measurements to determine oil-water ratio (OWR), performed on oil-based mud (OBM) drilling fluid. Thus, the drilling fluid must be conditioned to neutralize the fine particles of active clay prior to performing the electrical characterization tests.

In accordance with aspects of the present disclosure, apparatuses and methods are provided to neutralize the active clay contained in the OBM, transforming the active clay into electrically inert clay (referred to herein as inert clay). A sample of OBM may be incrementally titrated with a chemical, for example methylene blue, to displace the ions in the active clay and capacitance measurements performed after each incremental addition of the chemical. A stable capacitance measurement value obtain over several consecutive measurements indicates neutralization of the active clay effect as a reaction to the introduction of the chemical.

OWR for OBM is typically measured using a retort. The retort heats a known volume of OBM to a very high temperature to flash off the water and the oil. The water and oil is condensed and measured volumetrically to determine the OWR. Retorting to determine OWR takes approximately an hour. The above method can be performed in minutes, for example approximately 10 minutes, compared to conventional methods of measuring OBM capacitance that require hours to perform. The method may be automated and performed in real-time or near real-time. OBM may be pumped from the mud pit, samples measured out, titration and capacitance measurements as well as other characterization measurements performed, and results reported under computer control at regular time intervals in real-time or near real-time.

Drilling fluids are two-phase compounds: a fluid and solid phase. The character of the fluid phase is determined by chemically analyzing the concentrations of its constituents. The character of the solid phase is tested to determine solids concentration, specific densities, and particle sizes. Drilling fluids, also referred to as muds, are divided into two general types: water-based muds and oil-based muds (OBM).

Oil-based muds contain three phases: oil, brine, and solids phases. The oil phase is the continuous phase in which everything else in the system is mixed. The oil may be, for example, diesel, mineral oil, or a synthetic oil. The brine phase is a high concentration salt/water solution (e.g., using $CaCl_2$) or other such as glycols or other brines) that is emulsified into the oil. In some cases, water influx caused by formation water, added water for wellbore cleaning, etc., can become part of the drilling fluid reducing the salinity of the brine phase and upsetting the osmotic balance between the water in the OBM and the formation water with the undesirable result of water being forced into the formation. The solids phase includes the weight materials, viscosifiers such as organo-clays, fluid loss reducers, and lost circulation materials. The solids phase must remain oil wet (i.e., in contact with the oil phase rather than the water phase). If the solid phase becomes water wet (i.e., in contact with the water phase rather than the oil phase), the invert emulsion system may flip into a water continuous system with very high viscosities and gel strengths. In some cases these may plug the wellbore or cause excessive hydraulic pressures.

On a drilling rig, drilling fluid, or mud, is pumped from a tank or reservoir at the surface (i.e., the mud pit) through the drill string where it sprays out of nozzles on the drill bit, cleaning and cooling the drill bit in the process. The drilling fluid then carries the cuttings up an annular space between the drill string and the sides of the hole being drilled, up through the surface casing, and back to the surface. Cuttings are then filtered out, for example by shale shakers, and the drilling fluid returns to the mud pits. The drilling fluid may then be pumped back down and is continuously recirculated.

The drilling fluid in the mud pits may be periodically tested. Based on the test results, the drilling fluid may be treated to give it properties that optimize and improve drilling efficiency. Various characteristics of the drilling fluid may be tested, for example, density, viscosity, gel strength, specific gravity, electrical stability, fluid loss, water phase salinity (WPS), etc. Test results can be used as input to hydraulic models for predicting needed adjustments of the drilling fluid composition, for example, for drilling through different expected formations. Test results may also indicate the need to change operational conditions such as pump rate, rate of penetration (ROP) and surface treatment methods such as centrifuges and shakers.

One characteristic of the drilling fluid that can be tested is impedance, or more specifically, capacitance. Since water has a high dielectric constant, and hence high capacitance, it can be distinguished from oil or gas. The capacitance of the drilling fluid can therefore identify water, and the oil-water ratio (OWR) of oil-based muds can be determined from the capacitance measurements. Dielectric constant and capacitance has been well studied in the literature for two-phase systems of emulsion and suspension such as OBM.

Several hydraulic models have been developed to describe mixing rules for drilling fluid mixtures. A complex model may be developed for multi-phase system, such as drilling fluid having solid particles dispersed in a water-in-oil emulsion (i.e., oil-based-mud (OBM)). However, charged particles from fine solid particles of active clays too small to filter (e.g., cutting fines) are commonly observed in the OBM during drilling activity. The existence of the charged particles significantly affects the dielectric constant/capacitance measurement. In accordance with various aspects of the present disclosure, titration of the OBM with a solution, for example, but not limited to, methylene blue, may be used to neutralize the active clay in the OBM, transforming the active clay into inert clay, prior to performing capacitance and/or dielectric measurements, as well as other characterization measurements. Neutralizing the active clay can improve the correlation of the capacitance and/or dielectric measurements to the oil-water ratio (OWR) prediction of the hydraulic models.

FIG. 1 is a graph 100 illustrating capacitance measurements of an OBM sample containing no active clay according to various aspect of the present disclosure. An OBM sample containing no active clay was prepared in a laboratory, and the sample was titrated with methylene blue solution. Referring to FIG. 1, capacitance of the sample was measured at a frequency of 1 MHz for the sample titrated with methylene blue at concentrations from 0% to 4.5% by volume (vol %). As shown in FIG. 1, the capacitance measurement for the OBM sample containing no active clay was not significantly affected by the amount of methylene blue added.

Figure 2:
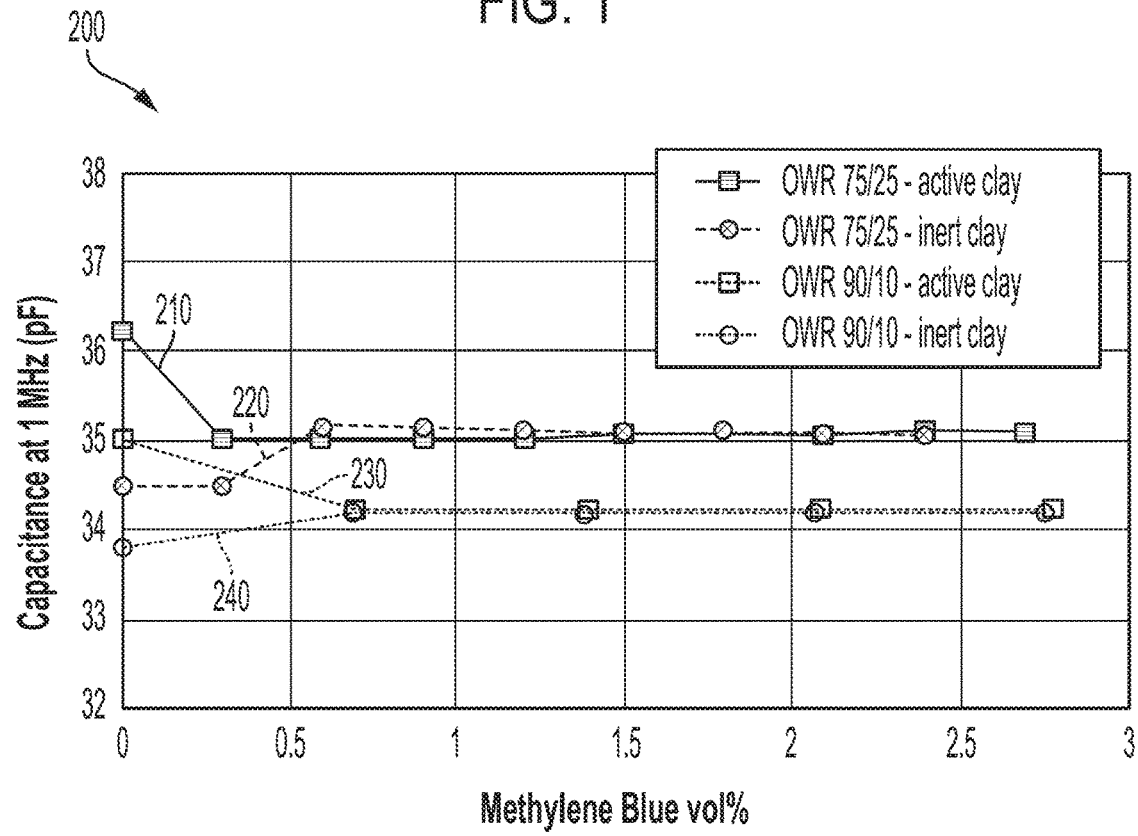
FIG. 2 is a graph illustrating capacitance measurements of OBM samples with and without active clay according to various aspects of the present disclosure.

FIG. 2 is a graph 200 illustrating capacitance measurements of OBM samples with and without active clay according to various aspect of the present disclosure. Capacitance measurements at a frequency of 1 MHz for four OBM samples prepared in a laboratory and titrated with methylene blue at concentrations from 0% to 3% by volume (vol %) are shown. A first plot 210 illustrates capacitance measurements for an OBM sample containing 10 ppb of active clay and having an OWR of 75/25. A second plot 220 illustrates capacitance measurements for an OBM sample containing only inert clay and having an OWR of 75/25. A third plot 230 illustrates capacitance measurements for an OBM sample containing 10 ppb of active clay and having an OWR of 90/10. A fourth plot 240 illustrates capacitance measurements for an OBM sample containing only inert clay and having an OWR of 90/10.

As can be seen in FIG. 2, before the titration with the methylene blue solution, the OBM samples having the same OWR show variations in their capacitance values. The variations are more pronounced for the samples containing active clay than for the samples containing only inert clay. By adding about 1 vol % of the methylene blue solution to each of the OBM samples, the capacitance values level off and remain constant at substantially the same values for the samples having the same OWR ratios. These results indicate the neutralization of the active clay effect (i.e., transforming the active clay into inert clay) on the OBM capacitance measurements as a reaction to the introduction of the methylene blue solution. Thus, by neutralizing the active clay a correlation between the capacitance measurements and the OWR may be determined and can be utilized to generate a compositional model for OWR prediction.

The titration and capacitance measurements of the present disclosure can be conducted in short period of time (e.g., minutes), compared to conventional retort techniques that require hours to complete. Thus, the disclosed titration and capacitance measurement techniques are applicable for automated real-time OWR measurements. Further, examples have been explained with respect to capacitance measurements of OBM. Other characterization measurements, for example, but not limited to, other impedance measurements or dielectric constant measurements, may be performed in a similar manner without departing from the scope of the present disclosure.

While the examples have been explained using methylene blue as the titrant, other solutions may be used to neutralize the effect of the active clays. For example, malachite green, crystal violet, or other chemicals capable of displacing the ions in the active material contained in the OBM may be used without departing from the scope of the present disclosure.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 3:
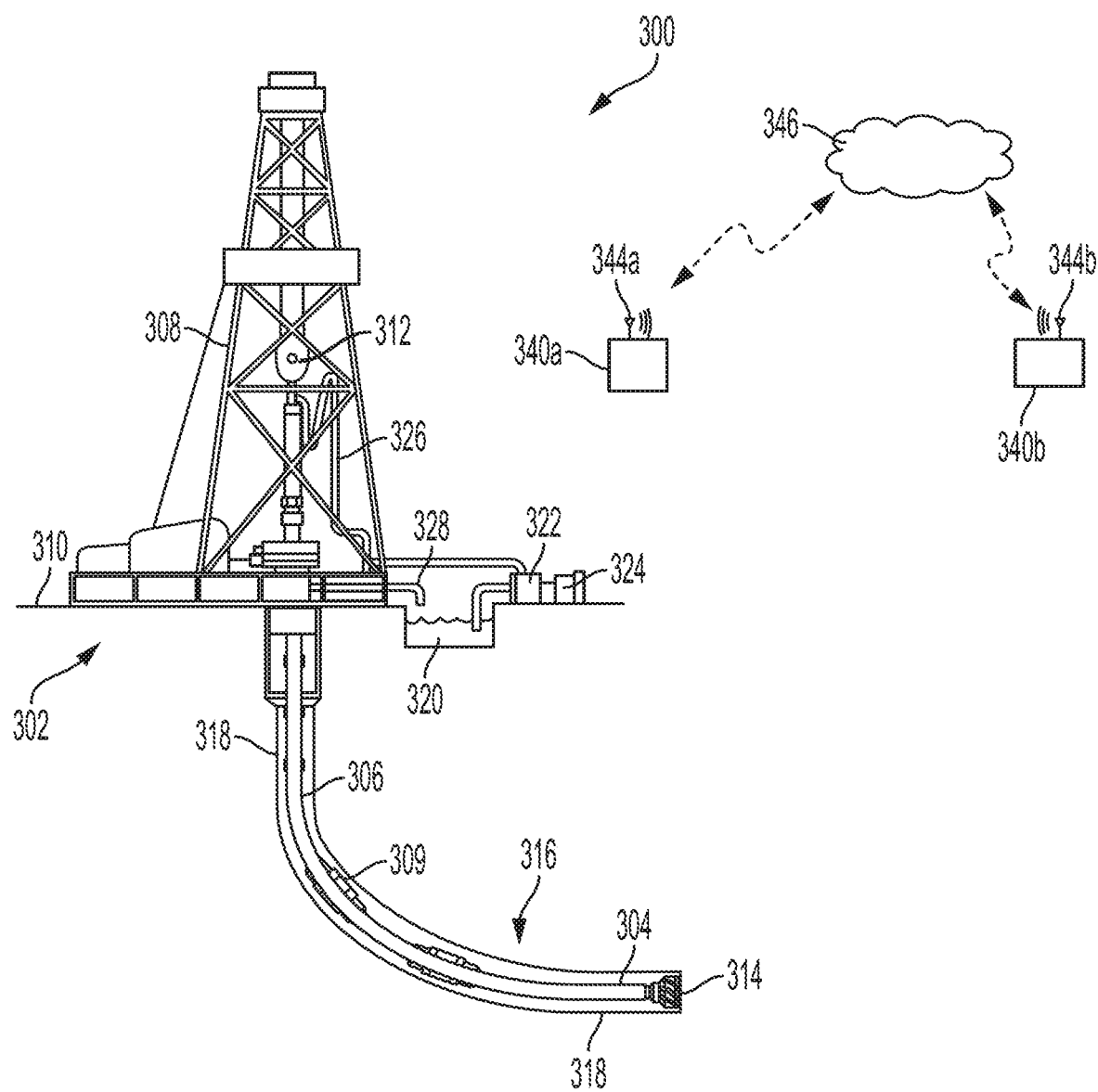
FIG. 3 is a cross-sectional side view of an example of a drilling system according to aspects of the present disclosure.

FIG. 3 is a cross-sectional side view of an example of a drilling system 300 according to aspects of the present disclosure. A wellbore of the type used to extract hydrocarbons from a formation may be created by drilling into the earth 302 using the drilling system 300. The drilling system 300 may be configured to drive a bottom hole assembly (BHA) 304 positioned or otherwise arranged at the bottom of a drillstring 306 extended into the earth 302 from a derrick 308 arranged at the surface 310. The derrick 308 includes a kelly 312 used to lower and raise the drillstring 306. The BHA 304 may include a drill bit 314 operatively coupled to a tool string 316, which may be moved axially within a drilled wellbore 318 as attached to the drillstring 306. Tool string 316 may include one or more tool joints 309. The combination of any support structure (in this example, derrick 308), any motors, electrical equipment, and support for the drillstring and tool string may be referred to herein as a drilling arrangement.

During operation, the drill bit 314 penetrates the earth 302 and thereby creates the wellbore 318. The BHA 304 provides control of the drill bit 314 as it advances into the earth 302. Drilling fluid, or "mud," from a mud tank 320 may be pumped downhole using a mud pump 322 powered by an adjacent power source, such as a prime mover or motor 324. The drilling fluid may be pumped from the mud tank 320, through a stand pipe 326, which feeds the drilling fluid into the drillstring 306 and conveys the drilling fluid to the drill bit 314. The drilling fluid exits one or more nozzles (not shown) arranged in the drill bit 314 and in the process cools the drill bit 314. After exiting the drill bit 314, the drilling fluid circulates back to the surface 310 via the annulus defined between the wellbore 318 and the drillstring 306, and in the process returns the drill cuttings and debris to the surface. The cuttings and drilling fluid mixture are passed through a flow line 328 and are processed such that a cleaned drilling fluid is returned down hole through the stand pipe 326 once again. Drilling fluid samples drawn from the mud tank 320 may be analyzed to determine the characteristics of the drilling fluid and any adjustments to the drilling fluid chemistry that should be made.

Sensors and/or instrumentation related to operation of the drilling system 300 may be connected to a computing device 340a. In various implementations, the computing device 340a may be deployed in a work vehicle, may be permanently installed with the drilling system 300, may be handheld, or may be remotely located. In some examples, the computing device 340a may process at least a portion of the data received and may transmit the processed or unprocessed data to a remote computing device 340b via a wired or wireless network 346. The remote computing device 340b may be offsite, such as at a data-processing center. The remote computing device 340b may receive the data, execute computer program instructions to analyze the data, and communicate the analysis results to the computing device 340a.

Each of the computing devices 340a, 340b may include a processor interfaced with other hardware via a bus. A memory, which may include any suitable tangible (and non-transitory) computer-readable medium, such as RAM, ROM, EEPROM, or the like, can embody program components that configure operation of the computing devices 340a, 340b. In some aspects, the computing devices 340a, 340b may include input/output interface components (e.g., a display, printer, keyboard, touch-sensitive surface, and mouse) and additional storage.

The computing devices 340a, 340b may include communication devices 344a, 344b. The communication devices 344a, 344b may represent one or more components that facilitate a network connection. In the example shown in FIG. 3, the communication devices 344a, 344b are wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In some examples, the communication devices 344a, 344b may use acoustic waves, surface waves, vibrations, optical waves, or induction (e.g., magnetic induction) for engaging in wireless communications. In other examples, the communication devices 344a, 344b may be wired and can include interfaces such as Ethernet, USB, IEEE 1394, or a fiber optic interface. The computing devices 340a, 340b may receive wired or wireless communications from one another and perform one or more tasks based on the communications.

Figure 4:
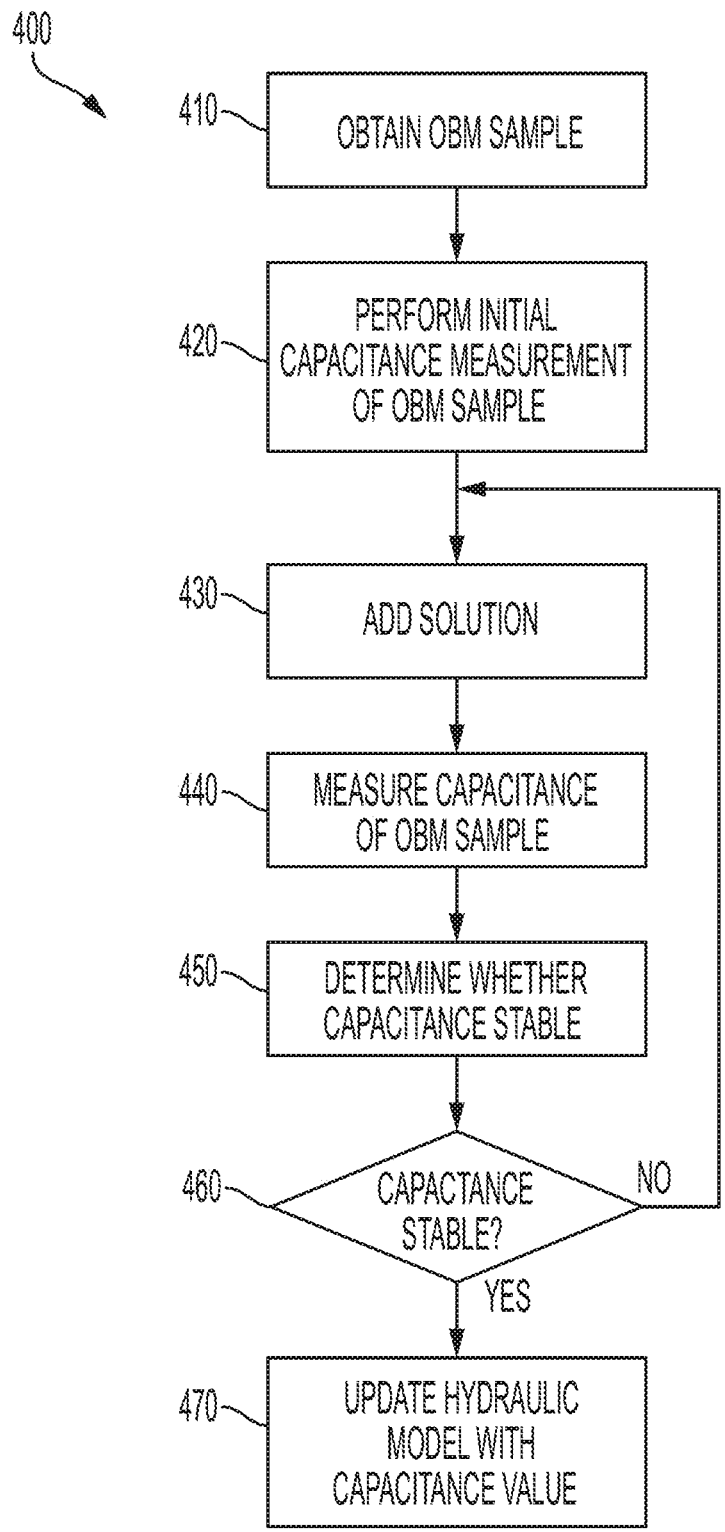
FIG. 4 is a flowchart illustrating a method for treating OBM to perform electrical characteristics measurements according to aspects of the present disclosure.

FIG. 4 is a flowchart illustrating a method 400 for treating OBM to perform electrical characteristics measurements according to aspects of the present disclosure. Referring to FIG. 4, at block 410, an OBM sample may be obtained. For example, an OBM sample may be drawn from the mud tank 320 or from the flowline 328. A timestamp may be recorded corresponding to the time the OBM sample was obtained. The OBM sample may be measured to obtain a known volume, for example, 100 ml or another volume, of OBM.

At block 420, an initial impedance measurement, for example a capacitance measurement, of the OBM sample as drawn from the mud tank 320 (i.e., including any active clays) may be performed. The impedance measurements may be performed using, for example, the measurement system illustrated in FIG. 5.

Figure 5:
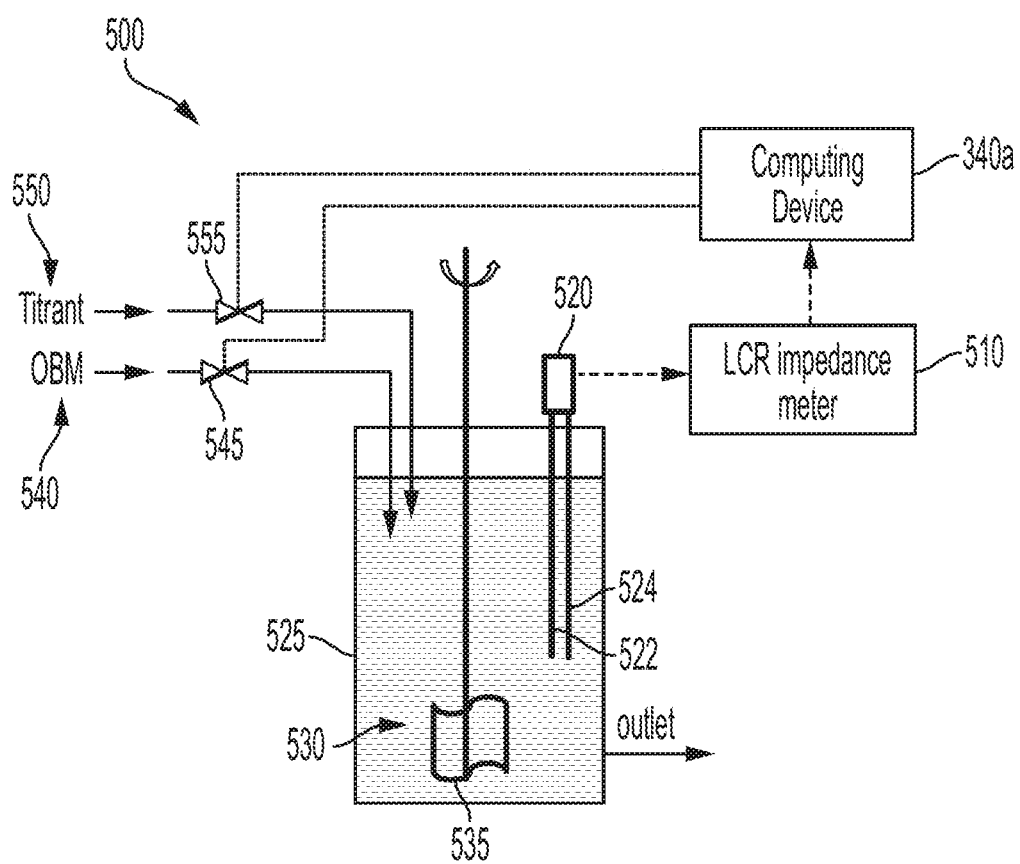
FIG. 5 is a block diagram illustrating an example of a measurement system for performing impedance measurements on an OBM sample according to various aspects of the present disclosure.

FIG. 5 is a block diagram illustrating an example of a measurement system 500 for performing electrical characterization measurements on an OBM sample according to various aspects of the present disclosure. Referring to FIG. 5, the measurement system 500 for performing electrical characterization measurements on an OBM sample may include an electrical characterization device, for example, an impedance analyzer 510 (e.g., an inductance-capacitance-resistance (LCR) analyzer), and an electrical characterization probe, for example, an impedance probe (e.g., a capacitance probe 520). The capacitance probe 520 may include two parallel plate electrodes 522 and 524 configured to permit the OBM to flow between the electrodes. According to various aspects of the present disclosure, the electrical characterization device may communicate with a computing device, for example the computing device 340a, and may receive instructions for performing measurements from the computing device 340a.

An OBM 540 sample may be drawn from the mud tank 320 or from the flowline 328, through a first valve 545. Operation of the first valve 545 may be controlled by the computing device 340a. The volume of the OBM 540 sample may be measured by, for example, but not limited to, a level sensor (not shown) configured to measure the level of the OBM 540 sample in a sample container 525 or with a pump stroke counter (not shown) configured to count pump strokes of a pump (not shown) that draws the OBM 540 from the mud tank 320 or from the flowline 328. The computing device 340a may operate the first valve 545 to admit OBM 540 to the sample container 525 until an appropriate volume, for example 100 ml or another volume, is reached. The appropriate volume may be indicated by a signal from the pump stroke counter or level sensor received by the computing device 340a. Other methods of measuring the sample volume may be used without departing from the scope of the present disclosure.

Titrant 550, for example, but not limited to methylene blue or another chemical having properties capable of neutralizing active clay (i.e., transforming the active clay into inert clay), may be introduced into the OBM 540 sample through a second valve 555. Operation of the second valve 555 may be controlled by the computing device 340a. The computing device 340a may control the second valve 555 to introduce the titrant 550 incrementally, for example in increments of 0.5 vol % or another incremental volume. The incremental volume of the titrant 550 may be measured by, for example, but not limited to, a pump stroke counter (not shown) configured to count pump strokes of a pump (not shown) that introduces the titrant 550. The pump stroke counter may provide a signal indicating a number of pump strokes to the computing device 340a, and the computing device 340a may determine an amount of titrant introduced based on a correlation between the signal indicating a number of pump strokes and knowledge of an amount of titrant 550 delivered per pump stroke. The OBM/titrant solution 530 may be continually mixed by an agitator 535 immersed in the sample container 525.

The capacitance probe 520 may be connected to the impedance analyzer 510 and immersed in the OBM 540 sample. Capacitance of the OBM/titrant solution 530 may be measured at a single frequency, for example, 1 MHz or another frequency, or may be measured over a frequency range, for example, 1 kHz to 1 MHz or another frequency range. The capacitance of the OBM/titrant solution 530 may be measured with no titrant 550 added to the OBM 540 sample and measured again after each incremental addition of the titrant 550. The addition of the titrant 550 may stop when the capacitance of the OBM/titrant solution 530 becomes stable.

The capacitance of the OBM/titrant solution 530 may be considered stable when the capacitance measurement at a given titrant 550 increment remains within a specified range, for example ±1% or another range, of capacitance values for capacitance measurements of the OBM/titrant solution 530 at one or more subsequent consecutive incremental titrant 550 additions. For example, if a first capacitance measurement is 35 pF at a titration increment of 1.0 vol % and a capacitance measurement after a next titration increment (e.g., 1.5 vol %) is within the specified range of 35 pF, the capacitance measurement may be considered stable. The oil-water ratio (OWR) of oil-based muds can be determined from the capacitance measurements. In some implementations, the impedance analyzer 510 may be in communication with the computing device 340a and/or the remote computing device 340b and may receive control commands from and may communicate the capacitance measurements to the computing device 340a and/or the remote computing device 340b. The capacitive measurements may be input to the compositional model to, at least in part, determine adjustments to the composition of the drilling fluid.

While FIG. 5 illustrates a capacitance probe as an impedance probe, other types of probes/sensors may be used to measure different electrical characteristics without departing from the scope of the present disclosure. In some implementations, the additional electrical characteristics may be measured after the capacitance of the OBM/titrant solution 530 solution becomes stable (i.e., after the active clays in the sample have been transformed into inert clay).

Returning to FIG. 4, at block 430, the OBM sample may be titrated. A known solution, for example, methylene blue or another solution, may be incrementally added, for example in increments of 0.5 ml or another increment, to the OBM sample. The increment may be optimized to determine characteristics of the OBM. Other chemicals capable of displacing the ions in the active material contained in the OBM may be used without departing from the scope of the present disclosure.

At block 440, after an incremental addition of solution to the OBM sample, capacitance of the OBM sample may be measured. For example, the capacitance may be measured using the measurement system illustrated in FIG. 5.

At block 450, it may be determined whether the capacitance of the OBM sample is stable. For example, the capacitance of the OBM sample may be determined to be stable when the capacitance measurements for two or another number of successive samples are within a predetermined range of one another. When the capacitance is stable, the OBM sample will be titrated, i.e., the active clay in the OBM sample will be transformed into inert clay.

The amount of solution necessary to titrate the OBM sample may be correlated to the amount of active clay contained in the OBM sample. Further, based on timestamps associated with each successive OBM sample, as well as knowledge of the lag time in bringing the sample to the surface of the well, the formation characteristics at the corresponding depth of the well may be determined.

When it is determined that the capacitance of the OBM sample is not stable (block 460—N), the process may continue at operation 440. When it is determined that the capacitance of the OBM sample is stable (block 460—Y), at block 470, the hydraulic model may be updated with the capacitance value for the OBM sample. For example, the impedance analyzer 510 may communicate that capacitance value(s) of the OBM sample to the computing device 340a and/or the remote computing device 340b. After the active clay in the OBM sample has been neutralized (i.e., transformed into inert clay), additional testing, for example, but not limited to, density, viscosity, specific gravity, etc., may be performed on the sample.

The method of FIG. 4 may be performed in minutes, for example approximately 10 minutes, compared to conventional retort methods of measuring the OWR of OBM that require hours to perform. In some implementations, the method of FIG. 4 may be automated and performed in real-time or near real-time. OBM may be pumped from the mud pit, samples measured out, titration and capacitance measurements as well as other characterization measurements performed, and results reported under computer control at regular time intervals in real-time or near real-time.

The specific operations illustrated in FIG. 4 provide a particular method for treating OBM to perform electrical measurements according to an example. Other sequences of operations may also be performed according to alternative examples. For example, alternative examples of the present invention may perform the operations outlined above in a different order. Moreover, the individual operations illustrated in FIG. 4 may include multiple sub-operations that may be performed in various sequences as appropriate to the individual operation. Furthermore, additional operations may be added or removed depending on the particular applications. Many variations, modifications, and alternatives may be recognized.

Figure 6:
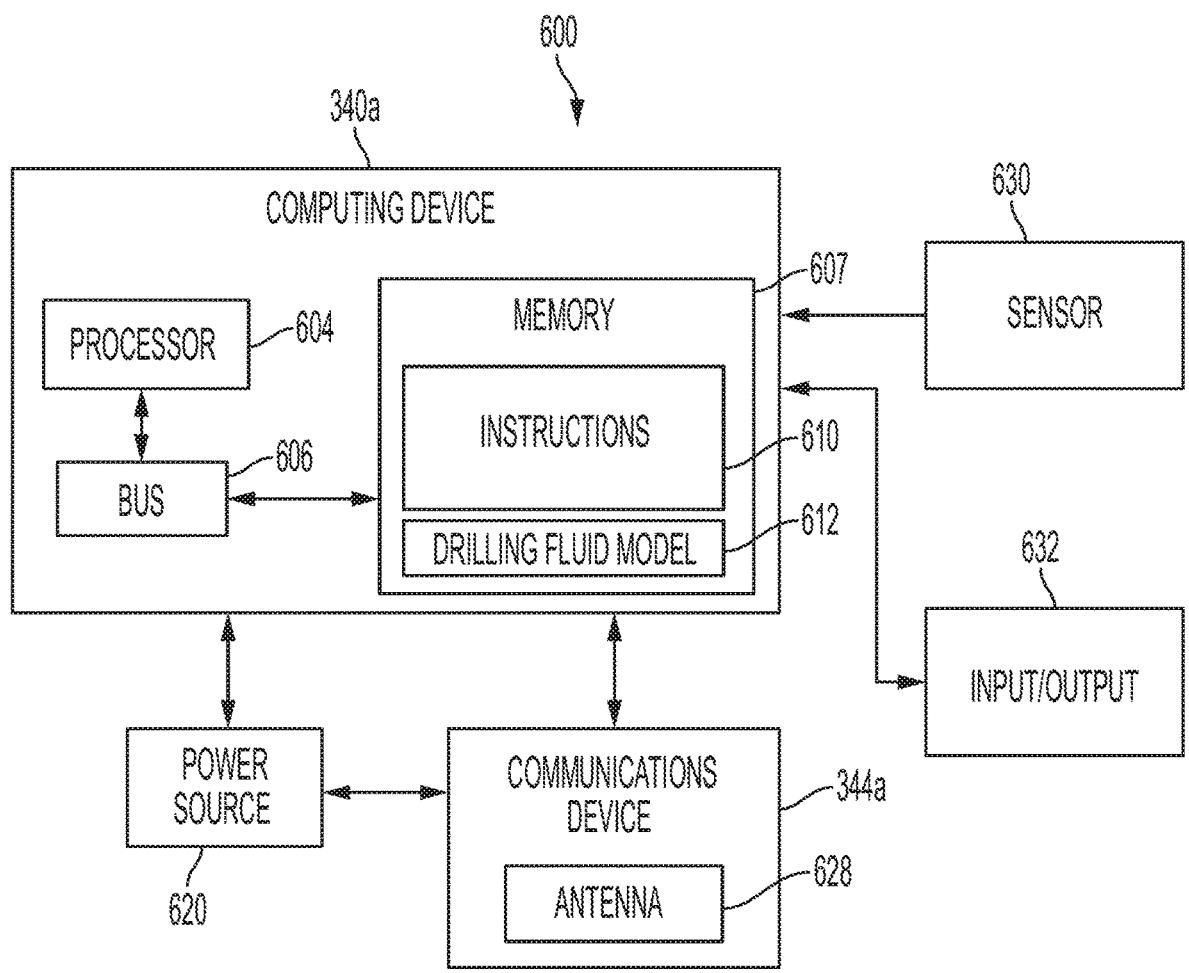
FIG. 6 is a block diagram of an example of a computing system 600 for analyzing and real-time monitoring of characteristics of drilling fluid according to aspects of the present disclosure.

FIG. 6 is a block diagram of an example of a computing system 600 for analyzing and real-time monitoring of characteristics of drilling fluid according to aspects of the present disclosure. In some examples, the components shown in FIG. 6 (e.g., the computing device 340a, power source 620, and communications device 344a) can be integrated into a single structure. For example, the components can be within a single housing. In other examples, the components shown in FIG. 6 can be distributed (e.g., in separate housings) and in electrical communication with each other.

The system 600 includes a computing device, for example, computing device 340a. The computing device 340a can include a processor 604, a memory 607, and a bus 606. The processor 604 can execute one or more operations for performing characterization measurements, including capacitance measurements to determine OWR of OBM, and providing data for an OBM prediction model. The processor 604 can execute instructions stored in the memory 607 to perform the operations. The processor 604 can include one processing device or multiple processing devices. Non-limiting examples of the processor 604 include a Field-Programmable Gate Array ("FPGA"), an application-specific integrated circuit ("ASIC"), a microprocessor, etc.

The processor 604 can be communicatively coupled to the memory 607 via the bus 606. The non-volatile memory 607 may include any type of memory device that retains stored information when powered off. Non-limiting examples of the memory 607 include electrically erasable and programmable read-only memory ("EEPROM"), flash memory, or any other type of non-volatile memory. In some examples, at least part of the memory 607 can include a medium from which the processor 604 can read instructions. A computer-readable medium can include electronic, optical, magnetic, or other storage devices capable of providing the processor 604 with computer-readable instructions or other program code. Non-limiting examples of a computer-readable medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C #, etc.

In some examples, the memory 607 can include computer program instructions 610 for automating a drilling fluid characteristics measurement process, for example, but not limited to some or all of the process operations described with respect to FIG. 4. These instructions 610 can also be usable for comparing measured drilling fluid chemistry to drilling fluid chemistry expected from a stored model 612 that predicts appropriate drilling fluid chemistry under various conditions. Computer program instructions 610 can also display predicted drilling fluid chemistry values or forward those values to other systems using communication device 344a, and handle control of any required signaling.

The system 600 can include a power source 620. The power source 620 can be in electrical communication with the computing device 340a and the communications device 344a. In some examples, the power source 620 can include a battery or an electrical cable (e.g., a wireline). In some examples, the power source 620 can include an AC signal generator. The computing device 340a can operate the power source 620 to apply a transmission signal to the antenna 628 to forward drilling fluid characterization data to other systems. For example, the computing device 340a can cause the power source 620 to apply a voltage with a frequency within a specific frequency range to the antenna 628. This can cause the antenna 628 to generate a wireless transmission. In other examples, the computing device 340a rather than the power source 620, can apply the transmission signal to the antenna 628 for generating the wireless transmission.

In some examples, part of the communications device 344a can be implemented in software. For example, the communications device 344a can include additional instructions stored in memory 607 for controlling the functions of communication device 344a. The communications device 344a can receive signals from remote devices and transmit data to remote devices (e.g., the remote computing device 340b of FIG. 1). For example, the communications device 344a can transmit wireless communications that are modulated by data via the antenna 628. In some examples, the communications device 344a can receive signals (e.g., associated with data to be transmitted) from the processor 604 and amplify, filter, modulate, frequency shift, and otherwise manipulate the signals. In some examples, the communications device 344a can transmit the manipulated signals to the antenna 628. The antenna 628 can receive the manipulated signals and responsively generate wireless communications that carry the data.

The computing system 600 can receive input from sensor(s) 630 operable to sense various characteristics of a drilling fluid. Computer system 600 in this example also includes input/output interface 632. Input/output interface 632 can connect to a keyboard, pointing device, display, and other computer input/output devices. An operator may provide input using the input/output interface 632. Drilling fluid characterization data or other data related to the operation of the system can also be displayed to an operator through a display that is connected to or is part of input/output interface 632.

In some aspects, a system and method for determining drilling fluid characteristics is provided according to one or more of the following examples. As used below, any reference to a series of examples is to be understood as a reference to each of those examples disjunctively (e.g., "Examples 1-4" is to be understood as "Examples 1, 2, 3, or 4").

Example 1 is a processing system including an electrical characterization device operable to measure an electrical parameter of a drilling fluid; a memory configured to store instructions; and a computing device operable to communicate with the electrical characterization device, the computing device configured to execute the instructions stored in the memory, the instructions, when executed, are operable to cause the processing system to measure a specified volume of a drilling fluid for a test sample; cause the electrical characterization device to measure an electrical parameter of the test sample; cause the processing system to add a chemical in known increments, the chemical formulated to effect a change in the electrical parameter of the test sample; after each incremental addition of the chemical, cause the electrical characterization device to measure the electrical parameter of the test sample; cause the electrical characterization device to determine that the electrical parameter measurement is at a stable value; and in response to determining that the electrical parameter measurement is at a stable value, correlate the stable value of the electrical parameter with an amount of water in the drilling fluid.

Example 2 is the system of example(s) 1, wherein the electrical parameter measurement is determined to be at a stable value when two or more consecutive measurement values of the electrical parameter fall within a specified range of each other.

Example 3 is the system of example(s) 1 and 2, wherein the computing device is further configured to execute instructions operable to determine adjustments to a composition of the drilling fluid based at least in part on the stable value of the electrical parameter.

Example 4 is the system of example(s) 1-3, wherein the drilling fluid is an oil-based mud (OBM), and the electrical parameter is impedance of the OBM.

Example 5 is the system of example(s) 1-4, wherein the computing device is further configured to correlate the stable value of the impedance of the oil-based mud to an oil-water ratio (OWR) of the OBM.

Example 6 is the system of example(s) 1-5, wherein the computing device is further configured to execute instructions operable to control a flow valve to admit the chemical for an amount of time based on a signal received from a pump stroke counter operable to count pump strokes of a pump that delivers the chemical.

Example 7 is the system of example(s) 1-6, wherein the chemical is methylene blue, malachite green, or crystal violet.

Example 8 is the system of example(s) 1-7, wherein the computing device is further configured to execute instructions operable to determine characteristics of different formations being drilled based on stable measurement values of the electrical parameter obtained for subsequent drilling fluid samples.

Example 9 is the system of example(s) 1-8, wherein the computing device is further configured to execute instructions operable to determine a water influx to a wellbore based on the stable measurement values of the electrical parameter obtained for subsequent drilling fluid samples.

Example 10 is the system of example(s) 1-9, wherein the computing device is further configured to execute instructions operable to input the stable value of the electrical parameter to a compositional model; and execute the compositional model to predict adjustments to a composition of the drilling fluid for drilling through expected formations.

Example 11 is a method, including measuring a specified volume of a drilling fluid for a test sample; measuring, with an electrical characterization device, an electrical parameter of the test sample; adding, in known increments, a chemical formulated to effect a change in the electrical parameter of the test sample; after each incremental addition of the chemical, measuring, with the electrical characterization device, the electrical parameter of the test sample; determining that the electrical parameter measurement is at a stable value; and in response to determining that the electrical parameter measurement is at a stable value, correlating the stable value of the electrical parameter with an amount of water in the drilling fluid.

Example 12 is the method of example(s) 11, wherein the electrical parameter measurement is determined to be at a stable value when two or more consecutive measurement values of the electrical parameter fall within a specified range of each other.

Example 13 is the method of example(s) 11 and 12, further including determining adjustments to a composition of the drilling fluid based at least in part on the stable value of the electrical parameter.

Example 14 is the method of example(s) 11-13, wherein the drilling fluid is an oil-based mud (OBM), and the electrical parameter is impedance of the OBM.

Example 15 is the method of example(s) 11-14, further including correlating the stable value of the impedance of the oil-based mud to an oil-water ratio (OWR) of the OBM.

Example 16 is the method of example(s) 11-15, wherein adding the chemical includes controlling a flow valve, wherein an amount of time the flow valve admits the chemical is based on a signal received from a pump stroke counter operable to count pump strokes of a pump that delivers the chemical.

Example 17 is the method of example(s) 11-16, wherein the chemical is methylene blue, malachite green, or crystal violet.

Example 18 is the method of example(s) 11-17, further including determining characteristics of different formations being drilled based on stable measurement values of the electrical parameter obtained for subsequent drilling fluid samples.

Example 19 is the method of example(s) 11-18, further including determining a water influx to a wellbore based on the stable measurement values of the electrical parameter obtained for subsequent drilling fluid samples.

Example 20 is the method of example(s) 11-19, further including inputting the stable value of the electrical parameter to a compositional model; and executing the compositional model to predict adjustments to a composition of the drilling fluid for drilling through expected formations.

The foregoing description of the examples, including illustrated examples, has been presented only for the purpose of illustration and description and is not intended to be exhaustive or to limit the subject matter to the precise forms disclosed. Numerous modifications, combinations, adaptations, uses, and installations thereof can be apparent to those skilled in the art without departing from the scope of this disclosure. The illustrative examples described above are given to introduce the reader to the general subject matter discussed here and are not intended to limit the scope of the disclosed concepts.

The invention claimed is:

1. A system, comprising:
a processing system including an electrical characterization device operable to measure an electrical parameter of a drilling fluid;
a memory configured to store instructions; and
a computing device operable to communicate with the electrical characterization device, the computing device configured to execute the instructions stored in the memory, the instructions, when executed, are operable to:
cause the processing system to measure a specified volume of a drilling fluid for a test sample;
cause the electrical characterization device to measure an electrical parameter of the test sample;
cause the processing system to add a chemical in known increments, the chemical formulated to effect a change in the electrical parameter of the test sample;
after each incremental addition of the chemical, cause the electrical characterization device to measure the electrical parameter of the test sample;
cause the electrical characterization device to determine that the electrical parameter measurement is at a stable value; and
in response to determining that the electrical parameter measurement is at a stable value, correlate the stable value of the electrical parameter with an amount of water in the drilling fluid.

2. The system of claim 1, wherein the electrical parameter measurement is determined to be at a stable value when two or more consecutive measurement values of the electrical parameter fall within a specified range of each other.

3. The system of claim 1, wherein the computing device is further configured to execute instructions operable to:
determine adjustments to a composition of the drilling fluid based at least in part on the stable value of the electrical parameter.

4. The system of claim 1, wherein:
the drilling fluid is an oil-based mud (OBM), and
the electrical parameter is impedance of the OBM.

5. The system of claim 4, wherein the computing device is further configured to correlate the stable value of the impedance of the oil-based mud to an oil-water ratio (OWR) of the OBM.

6. The system of claim 1, wherein the computing device is further configured to execute instructions operable to:
control a flow valve to admit the chemical for an amount of time based on a signal received from a pump stroke counter operable to count pump strokes of a pump that delivers the chemical.

7. The system of claim 1, wherein the chemical is methylene blue, malachite green, or crystal violet.

8. The system of claim 1, wherein the computing device is further configured to execute instructions operable to:
determine characteristics of different formations being drilled based on stable measurement values of the electrical parameter obtained for subsequent drilling fluid samples.

9. The system of claim 1, wherein the computing device is further configured to execute instructions operable to:
determine a water influx to a wellbore based on the stable measurement values of the electrical parameter obtained for subsequent drilling fluid samples.

10. The system of claim 1, wherein the computing device is further configured to execute instructions operable to:
input the stable value of the electrical parameter to a compositional model; and
execute the compositional model to predict adjustments to a composition of the drilling fluid for drilling through expected formations.

11. A method, comprising:
measuring a specified volume of a drilling fluid for a test sample;
measuring, with an electrical characterization device, an electrical parameter of the test sample;
adding, in known increments, a chemical formulated to effect a change in the electrical parameter of the test sample;
after each incremental addition of the chemical, measuring, with the electrical characterization device, the electrical parameter of the test sample;
determining that the electrical parameter measurement is at a stable value; and
in response to determining that the electrical parameter measurement is at a stable value, correlating the stable value of the electrical parameter with an amount of water in the drilling fluid.

12. The method of claim 11, wherein the electrical parameter measurement is determined to be at a stable value when two or more consecutive measurement values of the electrical parameter fall within a specified range of each other.

13. The method of claim 11, further comprising:
determining adjustments to a composition of the drilling fluid based at least in part on the stable value of the electrical parameter.

14. The method of claim 11, wherein:
the drilling fluid is an oil-based mud (OBM), and
the electrical parameter is impedance of the OBM.

15. The method of claim 14, further comprising correlating the stable value of the impedance of the oil-based mud to an oil-water ratio (OWR) of the OBM.

16. The method of claim 11, wherein adding the chemical comprises:
controlling a flow valve, wherein an amount of time the flow valve admits the chemical is based on a signal received from a pump stroke counter operable to count pump strokes of a pump that delivers the chemical.

17. The method of claim 11, wherein the chemical is methylene blue, malachite green, or crystal violet.

18. The method of claim 11, further comprising:
determining characteristics of different formations being drilled based on stable measurement values of the electrical parameter obtained for subsequent drilling fluid samples.

19. The method of claim 11, further comprising:
determining a water influx to a wellbore based on the stable measurement values of the electrical parameter obtained for subsequent drilling fluid samples.

20. The method of claim 11, further comprising:
inputting the stable value of the electrical parameter to a compositional model; and
executing the compositional model to predict adjustments to a composition of the drilling fluid for drilling through expected formations.

\* \* \* \* \*